Figure 1:
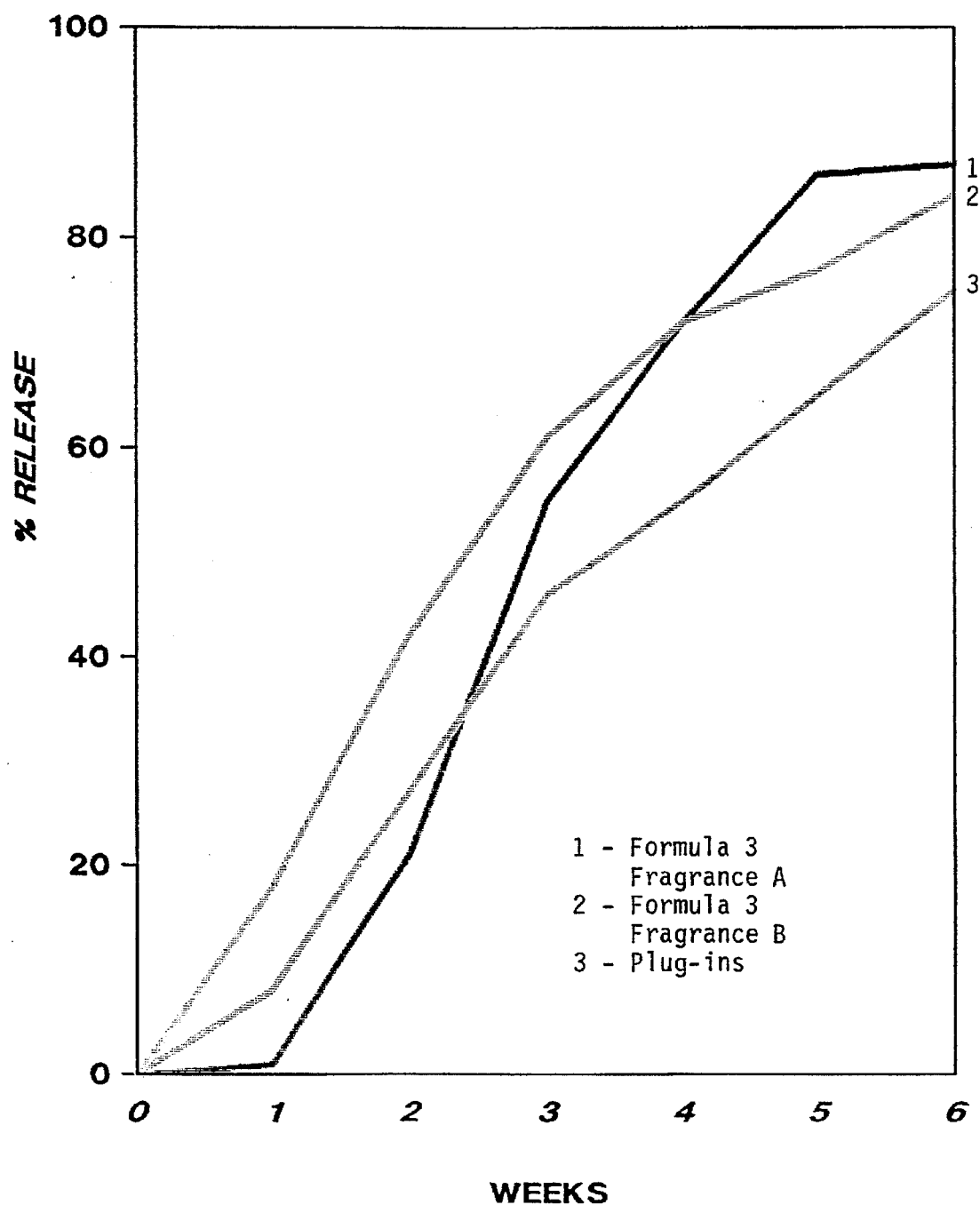

United States Patent [19]

Ansari et al.

[11] Patent Number: 5,643,866
[45] Date of Patent: Jul. 1, 1997

[54] AIR TREATING GEL

[75] Inventors: H. Rahman Ansari, Old Tappan, N.J.; Barbara Potts, Milford, Pa.

[73] Assignee: Quest International B.V., Bussum, Netherlands

[21] Appl. No.: 480,741

[22] Filed: Jun. 7, 1995

[51] Int. Cl.$^6$ .................................................. A61K 7/46
[52] U.S. Cl. ........................................ 512/4; 424/76.4
[58] Field of Search ............................. 512/4; 424/76.4

[56] References Cited

U.S. PATENT DOCUMENTS 4,617,147  10/1986  Shibanai ........................... 252/522 A
4,722,835   2/1988  Schamper et al. ..................... 424/66

OTHER PUBLICATIONS

Abstract of J59077859-A; May 1984.

*Primary Examiner*—James H. Reamer
*Attorney, Agent, or Firm*—Cushman Darby & Cushman, IP Group of Pillsbury Madison & Sutro, LLP

[57] ABSTRACT

An air treating gel composition comprising fragrance component, one or more glycols and dibenzylidene sorbitol acetal, the composition being free from alkaline salts and volatile organic solvents having a vapor pressure of $0.1 \times^{mm}$ or greater at 20° C.

12 Claims, 2 Drawing Sheets

AIR TREATING GEL

BACKGROUND OF THE INVENTION

A wide variety of air treating compositions, both gel and non-gel types, are in use today. While the available compositions may exhibit one or more useful features, each also generally has at least one undesirable property that may limit its use. In some instances, for example, the composition may include a volatile organic solvent or carrier which has a vapor pressure of $0.1 \times^{mm}$ or greater at 20° C. Such organic compounds, defined as VOC (volatile organic compounds), present environmental problems and are subject to regulation in many areas in the United States.

Gels have also been made from seaweed extracts (e.g. carrageenan). However, these can hold only small concentrations of fragrance oils. Furthermore, such products are not completely stable under elevated temperatures, are not transparent, and generally have poor active release characteristics. Sodium stearate based gels can hold more actives than carrageenans but are alkaline in nature and have stability problems at normally encountered elevated temperatures.

U.S. Pat. No. 4,617,147 discloses a solid perfume composition prepared by mixing together perfume oil, hydroxypropyl cellulose in alcohol solution, and a saturated solution of dibenzylidene sorbitol in N-methyl-2-pyrrolidone. While this composition offers certain advantages, it would be preferable, if possible, to avoid the use of solvents such as ethanol and N-methyl-2-pyrrolidone. Additionally, the gels of U.S. Pat. No. 4,617,147 are formed at ambient temperature and lack thermal stability.

Fragrance impregnated polyolefin systems have also been proposed. These products can hold 25–30% fragrance loads but do not efficiently release the fragrance into the air and do not have a visible end point.

Silica gels have also been proposed. While these are capable of holding high levels of fragrance oils, they do not form self-supporting structures thus leading to leakage and safety concerns.

Other gel deodorizing compositions or the like are shown in the following patent publications:

Japanese patent publications JP 62221355-A and JP 91063381-B disclose a gel fragrant deodorant composition comprising a blend of water, an alcohol, organic solvent, pigment, moisture retaining agent, dibenzylidene sorbitol, butane-diol and perfume.

Two other Japanese patent publications JP 59077859-A and JP 88064986-B disclose gelled fragrant deodorizing compositions containing dibenzylidene sorbitol, with methyl-methoxy-butanol or ethylene glycol monoethyl ether. The compositions are described as useful in, for example, vehicles, toilets, bathrooms or the like.

Japanese patent publications JP 63043666-A and JP 93060387-A disclose aromatic water-gel compositions containing dipropylene glycol alkyl ether and/or propylene glycol alkyl ether, gelling agent, perfume and water.

A gelated perfumed detergent composition comprising 12-hydroxystearic acid and/or benzylidene sorbitol, perfume, dye and surfactant is disclosed in JP 61083300-A while JP 62041661-A discloses a transparent hydrogel perfume agent for toilets, cars or the like prepared by blending carrageenan or agar, perfume, surfactant and water.

Other prior disclosures include:

JP 83025644-B and JP 48075731-A which describe gelled cosmetic products comprising dibenzol sorbitol, hydroxy propyl cellulose coloring agent and perfume while JP 60179064-A and JP 89031387-B describe gel-like perfume compositions comprising sodium behenate, a volatile terpene hydrocarbon and/or isoparaffin hydrocarbon, glycol monoether and/or ethanol, water and perfume.

EP 512770-A1 describes clear gelled stable transparent cosmetic compositions containing dibenzylidene monosorbitol mono-hydroxy alcohol(s).

GB 1243564-A discloses a transparent gel perfume which contains 8–30% primary, secondary, or tertiary phosphoric esters of 8–18 C. aliphatic alcohols, addition compounds of these alcohols with ethylene oxide or addition compounds of ethylene oxide with alkylphenols in which the alkyl group contains 8–16 C. atoms, or their mixtures. The esters are present in the form of their alkali or alkanolamine salts. The gelatinous transparent product is intended for application to the skin.

U.S. Pat. No. 4,722,835 describes a solid antiperspirant dibenzyl monosorbitol acetal gel containing a basic metal salt as stabilizer.

GB 1598449-A discloses air treatment gels, especially air freshener, containing soap, a monoalkyl ether of an alkylene glycol and one or more volatile air treatment compounds, e.g. a perfume.

Generally speaking, most, if not all, the prior air treating gel compositions include volatile organic solvents and/or alkaline salts which would preferably be avoided if an acceptable gel alternative free from such solvents and salts could be realized. The present invention provides such air treating gel compositions.

SUMMARY OF THE INVENTION

Briefly stated, the air treating gel of the invention is a crystal clear, self-supporting, highly concentrated composition which is free of undesirable volatile organic solvents and alkaline salts and is able to deliver a substantial fragrance payload over an extended period of time.

The product comprises, as essential components, one or more fragrance oils, one or more glycols and dibenzylidene sorbitol acetal (DBSA) as gelling agent. These components will normally be present in the following amounts on a percent by weight basis:

|  | % |
| --- | --- |
| fragrance oils | 1.0–88.5 |
| glycol(s) | 10.0–97.5 |
| DBSA | 1.5–4.0 |

Other components may also be included which do not affect the overall nature of the product. For example, water in amounts up to 45% by weight of the product may be used. Surfactants such as Igepol CO 630 in small amounts (e.g. 2–5%) may also be included.

The use of DBSA, as the gelling agent, together with one or more glycol solvents, is believed to be essential to the success of the invention. These two components can be combined to provide a self-supporting gel structure containing substantial fragrance which is controllably released in effective amount over a relatively long period, e.g. 6–8 weeks.

As indicated, the present composition is free from volatile organic compounds (VOC) and other components which are considered environmentally undesirable. The composition, as noted, is also free from alkaline salts and has an essentially neutral pH.

An advantage of the present product is that a wide range of fragrances may be used, particularly since the product is neutral and heat stable. A further advantageous feature of the gel is that it provides a visible use-up signal by undergoing appreciable shrinkage as the product reaches the end of its useful life. Additionally, the product is capable of holding and delivering a high payload of fragrance under various conditions.

Any conventional fragrance oil may be used for present purposes. This includes, for example, such fragrances as fresh, fruity, floral and woody type.

The amount of fragrance used can be widely varied as shown above but normally will not exceed 50-65% by weight of the composition and usually the amount of fragrance or fragrance mixture will be in the order of 10-50 parts by weight although an advantage of the present gel is that it can be loaded with an exceptionally high amount of fragrance.

The glycol component may comprise one or more simple glycols such as ethylene glycol or propylene glycol and/or an ether glycol, notably an alkylether glycol, such as diethylene glycol ethyl ether (Carbitol). Mixtures of two or more glycols can be used. The amount of glycol component can be varied, depending on other components, but usually will be in the range of 20.0-40.0% or higher on a weight basis.

The DBSA functions as the gelling agent and any effective amount thereof usually 1-10% by weight can be used provided the amount is sufficient under the other conditions of use to provide a self-supporting gel structurer.

The compositions of the invention may be prepared by mixing the components together and heating the mixture at, for example 80°-90° C., with agitation to cause complete solubilization of the DBSA gelling agent. On cooling at, for example, ambient temperature or below, a heat stable, shaped solid gel product is obtained which can withstand temperatures of up to 50°-60° C. without melting to a liquid.

The following are representative compositions according to the invention:

| Formula 1 | |
|---|---|
| Fragrance Oil | 10 parts |
| Carbitol[1] | 43 parts |
| Propylene Glycol | 20 parts |
| Water | 25 parts |
| DBSA | 2 parts |
| | 100 |

| Formula 2 | |
|---|---|
| Fragrance Oil | 10 parts |
| Carbitol | 28 parts |
| Propylene Glycol | 15 parts |
| DBSA | 2 parts |
| Igepal CO 630 | 5 parts |
| Water | 40 parts |
| | 100 |

| Formula 3 | |
|---|---|
| Fragrance Oil | 50 parts |
| Propylene Glycol | 48 parts |
| DBSA | 2 parts |
| | 100 |

The fragrance oil in the above compositions of formulas 1 and 2 was a fresh, fruity, floral and woody type whereas the formula 3 used a citrus, herbacious, lavender and woody type.

The above formulations were prepared as noted earlier, i.e. by mixing the ingredients together at 80°-90° with sufficient agitation to solubilize all of the ingredients. The resulting liquid was then be poured into appropriately shaped molds. The liquid gelled to a solid product within a few minutes (e.g. 2-20 minutes) at ambient temperature (20°-25° C.). The gelling point of the formulation will vary and is dependent on the solvent system and the fragrances which are used. Generally speaking, however, gelling occurs at temperatures below 70° C., e.g. 50°-60° C.

The gel composition of the invention can be used for freshening air in at least two distinct ways, i.e. as a dynamic freshener or as a static freshener. A dynamic freshener is an air freshener product in which the active, such as the fragrance in the present case, is assisted in its volatilization from the gel by heat. The thermally assisted vaporization of actives from the gel of the invention is the most preferred approach as the highly desirable and controlled release of fragrance and dramatic gel shrinkage to signal exhaustion of the fragrance actives can be best obtained with heat. This allows volatilization of fragrance ingredients as well as the glycol solvents such as propylene glycol. The ease with which these glycols are volatilized along with the fragrances was unexpected and surprising since the vapor pressure of the glycols is extremely low. However, this co-volatilization of glycols is highly beneficial in treating the air since glycols are well known for their low toxicity and mold growth inhibition, and are recognized by the US EPA as air sanitizers/disinfectants.

FIG. 1 illustrates the dynamic release profiles of products when tested in a commercially available "Airwaves" electrical unit. Gelled products representative of Formula 3 above using Fragrance A and Fragrance B were contained in different vessels (aluminum, polyolefin) with and without physical barriers to serve as rate control mechanisms. Curves 1 and 2 of FIG. 1 show the complete and efficient release of fragrance for the test compositions of the invention compared to a commercial "Airwaves" polyolefin system as shown by curve 3. It is also noted that the compositions represented by curves 1 and 2 showed a demonstrable end point (i.e. 98% shrinkage) compared with the total lack of visible change in the polyolefin formulation represented by curve 3.

Static air fresheners are air freshener products that function under ambient conditions without any assistance from heat or forced air circulation. Such consumer products are exemplified by commercial products such as "Stick-ups" and "Renuzit Adjustable Gel Air Fresheners." Currently available products are generally less than satisfactory in regard to product longevity and uniformity of the fragrance character or hedonics.

Figure 2:
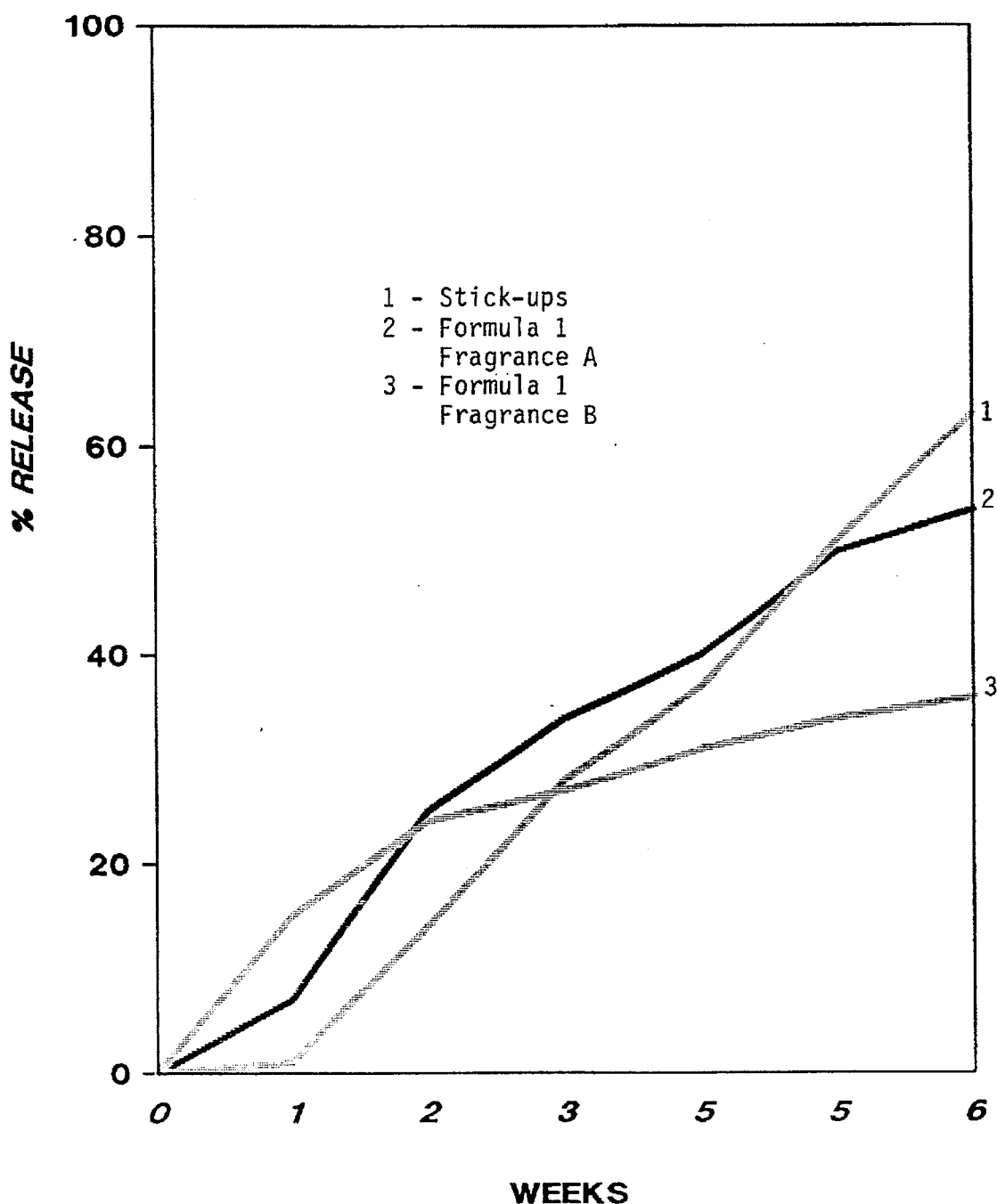

However, the present invention overcomes most of the above mentioned problems and provides a composition which can last up to eight weeks, perfuming the environment in a consistent manner. FIG. 2 compares two products according to Formula 1 of the invention with an available "Stick-ups" product. The significantly higher release of fragrance over a longer period of time is evident from FIG. 2.

Fragrance A and Fragrance B, as used in the tests referred to above are, respectively, fresh, fruity, floral, woody and citrus, herbacious, lavender, woody. Advantages of the gel compositions of the invention include the following:

(1) the product is a solid form air freshener which does not suffer from problems caused by leaks or spills as would occur with liquid formulations;

(2) the product is also transparent, clear and attractive;
(3) it is highly concentrated in terms of fragrance loading, for example, the product may have 75–80% fragrance loading;
(4) controlled fragrance release is obtained for over 6–8 weeks;
(5) the product is free from VOC as defined by CARB (Californian Air Resources Board);
(6) there is a distinct end point with greater than 90% shrinkage when the product life is exhausted; and
(7) the product is stable, free from alkaline salts and has a neutral pH.

Other features and advantages of the invention will be evident to those skilled in the art. Additionally, it will be appreciated from the foregoing that various modifications may be made in the invention as described above. Accordingly, the scope of the invention is defined in the following claims wherein:

What is claimed is:

1. An air treating gel composition comprising, on a weight basis:

| | |
|---|---|
| fragrance oil | 1.0–88.5% |
| glycol component | 10.0–97.5% |
| dibenzylidene sorbitol acetal | 1.5–10.0% | the composition being free from alkaline salts and volatile organic solvents having a vapor pressure of $0.1\times^{mm}$ or greater at 20° C.

2. A gel composition according to claim 1 which is a crystal clear, self-supporting molded composition.

3. A gel composition according to claim 2 wherein the glycol component is at least one member of the group consisting of diethylene glycol monoethyl ether and propylene glycol.

4. A gel composition according to claim 3 including from 20–50% by weight of water.

5. A gel composition according to claim 1 consisting essentially of in parts by weight:

| | |
|---|---|
| fragrance oil | 10 parts |
| diethylene glycol monoethyl ether | 43 parts |
| propylene glycol | 20 parts |
| water | 25 parts |
| DBSA | 2 parts |

6. A gel composition according to claim 1 consisting essentially of in parts by weight:

| | |
|---|---|
| fragrance oil | 10 parts |
| diethylene glycol monothethyl ether | 28 parts |
| propylene glycol | 15 parts |
| DBSA | 2 parts |
| Igepal CO 6730 | 5 parts |
| water | 40 parts |

7. A gel composition according to claim 1 consisting essentially in parts by weight:

| | |
|---|---|
| fragrance oil | 50 parts |
| propylene glycol | 48 parts |
| DBSA | 2 parts. |

8. A gel composition according to claim 1 containing 1.5–4.0% w/w of dibenzyl sorbitol acetal.

9. A gel composition according to claim 1 containing 10–65% w/w of fragrance oils.

10. A gel composition according to claim 1 containing at least 20% 2/2 of glycol component.

11. A gel composition according to claim 1 additionally comprising up to 45% by weight of water.

12. A gel composition according to claim 1 which has a neutral pH.

* * * * *